(12) United States Patent
Bostick et al.

(10) Patent No.: US 10,952,673 B2
(45) Date of Patent: *Mar. 23, 2021

(54) INSTANT MESSAGING STATUS REPORTING BASED ON SMART WATCH ACTIVITY (71) Applicant: INTERNATIONAL BUSINESS MACHINES CORPORATION, Armonk, NY (US)

(72) Inventors: James E. Bostick, Cedar Park, TX (US); John M. Ganci, Jr., Raleigh, NC (US); Martin G. Keen, Cary, NC (US); Sarbajit K. Rakshit, Kolkata (IN)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 45 days.

This patent is subject to a terminal disclaimer.

(21) Appl. No.: 16/205,845

(22) Filed: Nov. 30, 2018

(65) Prior Publication Data
US 2019/0099128 A1 Apr. 4, 2019

Related U.S. Application Data (63) Continuation of application No. 14/940,419, filed on Nov. 13, 2015, now Pat. No. 10,231,668.

(51) Int. Cl.
*A61B 5/00* (2006.01)
*A61B 5/0205* (2006.01)
(Continued)

(52) U.S. Cl.
CPC ............ *A61B 5/681* (2013.01); *A61B 5/0205* (2013.01); *A61B 5/1112* (2013.01);
(Continued)

(58) Field of Classification Search
CPC .............. A61B 55/681; A61B 55/0205; A61B 55/1112; A61B 55/1116; H04L 51/04; H04L 51/043; H04L 51/046
See application file for complete search history.

(56) References Cited

U.S. PATENT DOCUMENTS 7,548,756 B2    6/2009   Velthuis et al.
8,082,302 B2   12/2011   Becker et al.
(Continued)

FOREIGN PATENT DOCUMENTS

EP    2860686 A1    4/2015

OTHER PUBLICATIONS

Shih et al., "Use and Adoption Challenges of Wearable Activity Trackers", iConference Proceedings, Mar. 2015, 12 pages.
(Continued)

*Primary Examiner* — Shirley X Zhang
(74) *Attorney, Agent, or Firm* — Brian Restauro; Andrew D. Wright; Roberts Calderon Safran & Cole, P.C.

(57) ABSTRACT

Systems and methods for determining an instant messaging (IM) status of a user wearing a smart watch are disclosed. A computing device includes: a processor; a memory; and sensors including at least one biometric sensor, at least one location sensor, and at least one orientation sensor. The memory stores a status application that is executed by the processor and is configured to: obtain real time data from at least one of the sensors; determine an instant messaging (IM) status based on the real time data; and transmit the IM status to a server for providing to other IM users.

20 Claims, 4 Drawing Sheets (51) Int. Cl.
*H04L 12/58* (2006.01)
*H04W 4/029* (2018.01)
*A61B 5/11* (2006.01)

(52) U.S. Cl.
CPC ............ *A61B 5/1116* (2013.01); *H04L 51/04* (2013.01); *H04L 51/043* (2013.01); *H04L 51/046* (2013.01); *H04W 4/029* (2018.02); *A61B 2562/0219* (2013.01)

(56) References Cited

U.S. PATENT DOCUMENTS

| | | | |
|---|---|---|---|
| 8,644,807 B2 | 2/2014 | Wisebourt et al. | |
| 8,725,842 B1 | 5/2014 | Al-Nasser | |
| 8,781,431 B2 | 7/2014 | Pelton et al. | |
| 8,811,951 B1* | 8/2014 | Faaborg | H04M 1/57 455/411 |
| 8,954,290 B2 | 2/2015 | Yuen et al. | |
| 9,033,875 B2 | 5/2015 | Teller et al. | |
| 9,083,600 B1 | 7/2015 | Smith et al. | |
| 9,229,535 B2 | 1/2016 | Vice et al. | |
| 9,817,948 B2 | 11/2017 | Swank | |
| 10,148,778 B2* | 12/2018 | Lee | H04L 67/26 |
| 10,401,807 B2 | 9/2019 | Jo et al. | |
| 2005/0262195 A1 | 11/2005 | Ono et al. | |
| 2006/0248184 A1 | 11/2006 | Wu et al. | |
| 2009/0113311 A1 | 4/2009 | Fried et al. | |
| 2009/0300525 A1* | 12/2009 | Jolliff | H04L 67/306 715/764 |
| 2010/0127921 A1 | 5/2010 | Chen et al. | |
| 2011/0183645 A1* | 7/2011 | Chawla | H04M 3/42357 455/410 |
| 2012/0005277 A1 | 1/2012 | O'Sullivan et al. | |
| 2012/0009900 A1 | 1/2012 | Chawla | |
| 2012/0054279 A1 | 3/2012 | Dantec et al. | |
| 2012/0239767 A1 | 9/2012 | Deluca | |
| 2013/0072765 A1 | 3/2013 | Kahn et al. | |
| 2013/0086602 A1 | 4/2013 | Mikan et al. | |
| 2013/0237287 A1 | 9/2013 | Ferren et al. | |
| 2014/0006163 A1 | 1/2014 | Sengupta et al. | |
| 2014/0135612 A1 | 5/2014 | Yuen et al. | |
| 2014/0221020 A1 | 8/2014 | Xie et al. | |
| 2014/0276244 A1 | 9/2014 | Kamyar | |
| 2015/0119726 A1 | 4/2015 | Matsuno et al. | |
| 2017/0135635 A1 | 5/2017 | Bostick et al. | |

OTHER PUBLICATIONS

Ens et al., "Candid Interaction: Revealing Hidden Mobile and Wearable Computing Activities", UIST 2015, Charlotte NC, Nov. 8, 2011, 10 pages.

Anonymous, "Ignore Facebook Messenger's "active now" or "on line" presence info, it's inaccurate", https://jdrch.wordpress.com/2013/04/ 8/ignore-facebook-messengers-active-now-or-on line-presence-infoits-inaccurate/, Apr. 18, 2013, 2 pages.

Hong et al., "ConaMSN: A context-aware messenger using dynamic Bayesian networks with wearable sensors", 2010, 7 pages.

Miluzzo et al., "CenceMe—Injecting Sensing Presence into Social Networking Applications", 2007, 28 pages.

"Context-Aware Technologies, Systems and Applications", 2009, 32 pages.

List of IBM Patents or Patent Applications Treated as Related, dated Nov. 26, 2018, 1 page.

* cited by examiner

INSTANT MESSAGING STATUS REPORTING BASED ON SMART WATCH ACTIVITY

BACKGROUND

The present invention relates generally to wearable computing devices and, more particularly, to instant messaging status reporting based on smart watch activity.

Instant Messaging (IM) systems, such as Facebook® Messenger, Skype®, and WhatsApp®, and corporate IM systems, allow users to set a status indicating their availability. IM status can be set in two ways: automated or manual. An automated status is set automatically by the IM system. Values such as "Active", "Away" are determined by user activity (e.g., whether the user has moved their mouse, opened the app, etc., within a given period of time). Values such as "In a Meeting" are set by integrating with resources such as a user's calendar. A manual status is set manually by the user.

The primary purpose of IM status is to inform message senders of the availability of the message recipient. It allows message senders to answer questions such as "is this a good time to send a message to this person?" and "how likely is it I will receive a response from this person right now?" Oftentimes the IM status assigned to a given user is a poor indicator of their true availability. A person with an IM status of "Active" might actually be busy performing other tasks. A person with a status of "Away" might quickly become active when they receive a message notification. Using only user activity and integration with resources such as calendars is insufficient for accurate IM status reporting.

Current IM status reporting is notoriously inaccurate as it uses only a few unreliable factors to determine what a given user is currently doing. This presents a problem to IM message senders, who do not know if potential recipients are truly available or not. With smart watches the problem is worse as the recipient appears to always be online and available, as notifications can always be received and displayed by their smart watch.

SUMMARY

In an aspect of the invention, there is a computing device including: a processor; a memory; and sensors including at least one biometric sensor, at least one location sensor, and at least one orientation sensor. The memory stores a status application that is executed by the processor and is configured to: obtain real time data from at least one of the sensors; determine an instant messaging (IM) status based on the real time data; and transmit the IM status to a server for providing to other IM users.

In another aspect of the invention, there is a computer-implemented method that includes: receiving, by a computing device, a first instant messaging (IM) status of a first user, wherein the first IM status is based on data obtained from at least one sensor of a smart watch; converting, by the computing device, the first IM status to a second IM status based on a status rule defined by the first user; and transmitting, by the computing device, the second IM status to a computing device of a second user.

In another aspect of the invention, there is a computer program product for determining an instant messaging (IM) status of a user wearing a smart watch. The computer program product includes a computer readable storage medium having program instructions embodied therewith. The program instructions executable by a computing device to cause the computing device to: obtain real time data from sensors of smart watch, wherein the sensors include at least one biometric sensor, at least one location sensor, and at least one orientation sensor; determine an IM status of the user based on the real time data; and transmit the IM status to a server for providing to other IM users.

BRIEF DESCRIPTION OF THE DRAWINGS

The present invention is described in the detailed description which follows, in reference to the noted plurality of drawings by way of non-limiting examples of exemplary embodiments of the present invention.

DETAILED DESCRIPTION

The present invention relates generally to wearable computing devices and, more particularly, to instant messaging status reporting based on smart watch activity. Aspects of the invention are directed to optimizing instant messaging (IM) interactions on a smart watch whereby the IM status of the smart watch wearer reflects the actual activity or state of mind of the user. In embodiments, IM status for a user is set to dynamically reflect the user's current activity (e.g., walking, sleeping, driving, etc.). In aspects, the IM status is reported to the IM contacts of the user through an IM status reporting matrix, providing the IM contacts with an indication of whether a given moment is a good time to send the user an instant message.

The emergence of smart watches brings IM messages directly to a recipient's wrist. The smart watch, which is typically worn all day and always online, alerts its wearer to incoming IM messages through notifications displayed on the watch, and through haptic feedback applied to the wrist. In addition to making the smart watch wearer easier to reach using IM, the smart watch brings the opportunity for better IM status reporting. Aspects of the invention utilize sensors fitted to smart watches to provide more accurate IM status reporting, making it easier for a message sender to know when the right time is to send somebody an IM message, and—equally importantly—when not to send one.

According to aspects of the invention, a smart watch is fitted with biometric, location, and orientation sensors that capture real-time sensor data on a continual basis from a user. In embodiments, this sensor data is persisted to create a historical record of sensor data. In implementations, an IM status application monitors the real-time smart watch sensors and historical sensor data and compares this data to a rules engine to determine what to set the user's current IM status to. Status can be generic (e.g. Active, Away, etc.) or specific (e.g., Driving, Walking, Stressed, etc.). In embodiments, an IM server receives the user's status and passes this status to the IM contacts of the user, using a status reporting matrix to determine which IM contacts see which IM status for a given user. The process is repeated as the user's IM status changes over time. Aspects thus include analysis of real-time smart watch biometric, location, and orientation data combined with historical sensor records to determine what a user is currently doing, and to assign an instant messaging status that represents this user activity through use of a rules engine. Aspects further include use of an instant messaging status reporting matrix to determine the granularity of instant messaging status shared with specific contacts, and to determine which instant messaging contacts can and cannot send messages to a recipient at a given time based upon this status.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowcharts and block diagrams in the Figures illustrate the architecture, functionality, and operation of possible implementations of systems, methods, and computer program products according to various embodiments of the present invention. In this regard, each block in the flowcharts may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the flowchart illustrations, and combinations of blocks in the flowchart illustrations, can be implemented by special purpose hardware-based systems that perform the specified functions or acts or carry out combinations of special purpose hardware and computer instructions.

Figure 1:
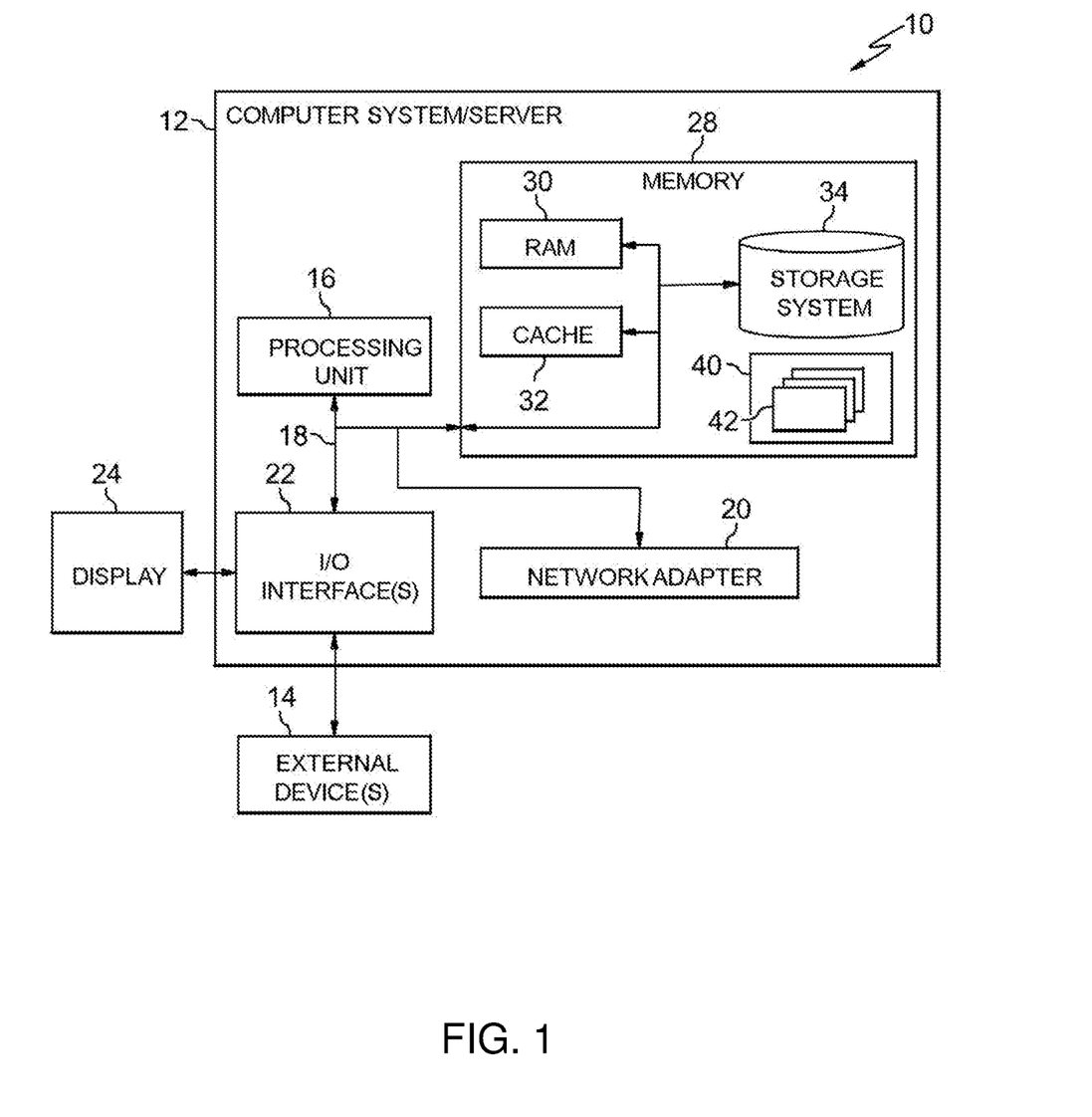
FIG. 1 depicts a computing infrastructure according to an embodiment of the present invention.

Referring now to FIG. 1, a schematic of an example of a computing infrastructure is shown. Computing infrastructure 10 is only one example of a suitable computing infrastructure and is not intended to suggest any limitation as to the scope of use or functionality of embodiments of the invention described herein. Regardless, computing infrastructure 10 is capable of being implemented and/or performing any of the functionality set forth hereinabove.

In computing infrastructure 10 there is a computer system (or server) 12, which is operational with numerous other general purpose or special purpose computing system environments or configurations. Examples of well-known computing systems, environments, and/or configurations that may be suitable for use with computer system 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system 12 may be described in the general context of computer system executable instructions, such as program modules, being executed by a computer system. Generally, program modules may include routines, programs, objects, components, logic, data structures, and so on that perform particular tasks or implement particular abstract data types. Computer system 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system 12 in computing infrastructure 10 is shown in the form of a general-purpose computing device. The components of computer system 12 may include, but are not limited to, one or more processors or processing units (e.g., CPU) 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 12 typically includes a variety of computer system readable media. Such media may be any available media that is accessible by computer system 12, and it includes both volatile and non-volatile media, removable and non-removable media.

System memory 28 can include computer system readable media in the form of volatile memory, such as random access memory (RAM) 30 and/or cache memory 32. Computer system 12 may further include other removable/non-removable, volatile/non-volatile computer system storage media. By way of example only, storage system 34 can be provided for reading from and writing to a nonremovable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system 12 may also communicate with one or more external devices 14 such as a keyboard, a pointing device, a display 24, etc.; one or more devices that enable a user to interact with computer system 12; and/or any devices (e.g., network card, modem, etc.) that enable computer system 12 to communicate with one or more other computing devices. Such communication can occur via Input/Output (I/O) interfaces 22. Still yet, computer system 12 can communicate with one or more networks such as a local area network (LAN), a general wide area network (WAN), and/or a public network (e.g., the Internet) via network adapter 20. As depicted, network adapter 20 communicates with the other components of computer system 12 via bus 18. It should be understood that although not shown, other hardware and/or software components could be used in conjunction with computer system 12. Examples, include, but are not limited to: microcode, device drivers, redundant processing units, external disk drive arrays, RAID systems, tape drives, and data archival storage systems, etc.

Figure 2:
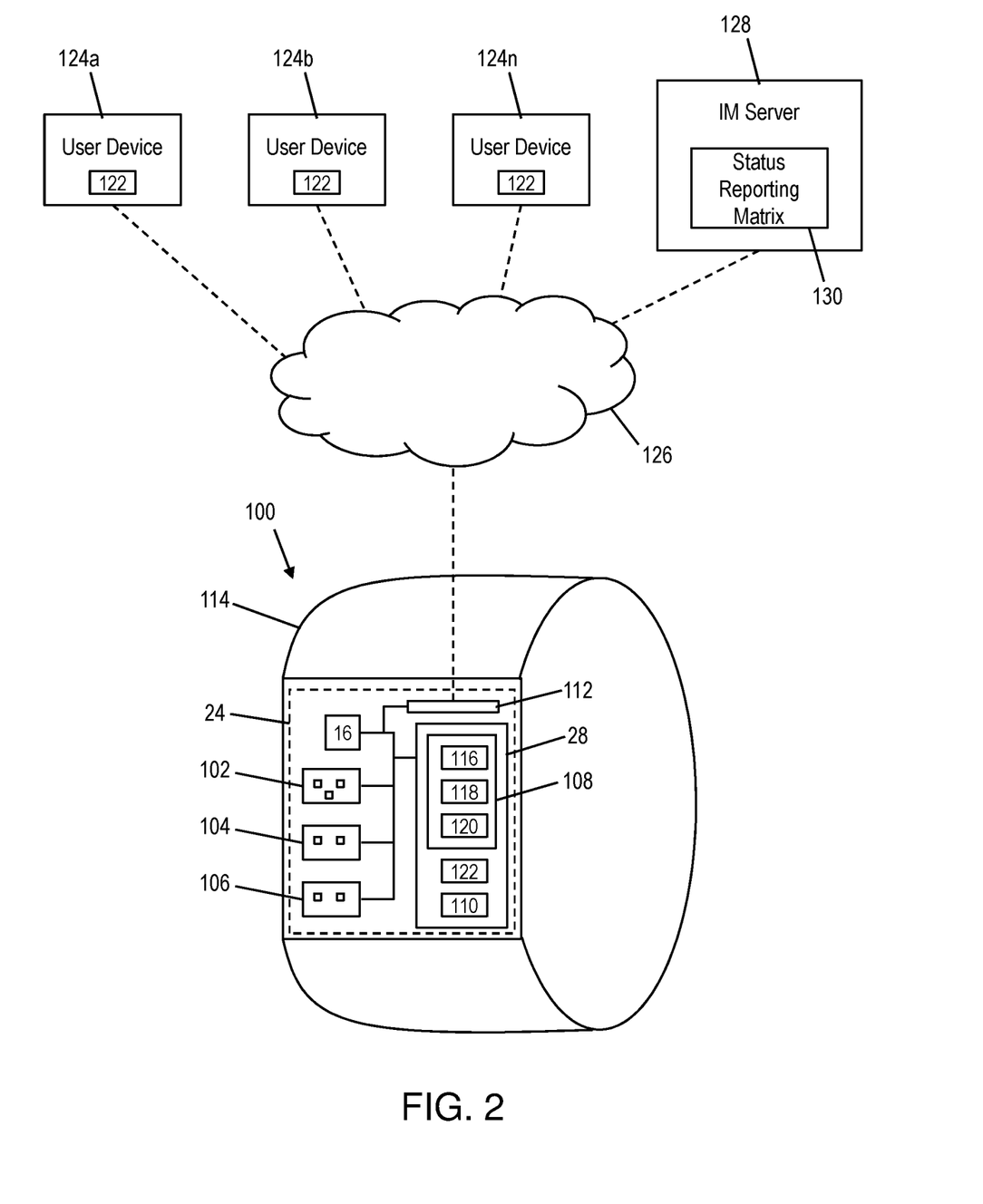
FIG. 2 shows an exemplary environment in accordance with aspects of the invention.

FIG. 2 shows an exemplary environment in accordance with aspects of the invention. In embodiments, a smart watch 100 includes sensors 102, 104, 106 and a status application 108. The smart watch 100 may be a wearable computing device and may be implemented using the computer system 12 of FIG. 1 or another suitable computing device. For example, the smart watch 100 may comprise a processing unit 16, a memory 28, and a display 24. The memory 28 may include mass storage 110 for storing large amounts of data in a persisting and machine-readable fashion. The memory 28 may also store mobile applications including a status application 108 that is executed by the processing unit 16. The display 24 may comprise a touch screen display that outputs an electronic visual display and that receives user input via stylus and/or finger touch. The smart watch 100 may also include at least one antenna 112 configured for wireless communication via at least one of cellular, WiFi, Bluetooth, and near field communication (NFC). The smart watch 100 may also include a wristband 114 and integrated devices such as a camera, audio speaker, microphone, and rechargeable battery.

According to aspects of the invention, the sensors include at least one biometric sensor 102, at least one location sensor 104, and at least one orientation sensor 106. In embodiments, the biometric sensors 102 are devices that monitor physiological aspects of the person wearing the smart watch 100. The biometric sensors 102 may include at least one of a heart rate monitor, a blood pressure monitor, and a stress level monitor. In embodiments, the location sensors 104 are devices that detect, and optionally track, a location of the smart watch 100. The location sensors 104 may include a compass sensor that detects a directional orientation of the smart watch 100 and a global positioning system (GPS) sensor that measures a location and speed of travel of the smart watch 100. In embodiments, the orientation sensors 106 are devices that detect how the smart watch 100 is moving in space. The orientation sensors 106 may include an accelerometer and a gyroscope.

Still referring to FIG. 2, the status application 108 may be a computer program/utility 40 as described with respect to FIG. 1, and in particular may be a mobile app. The status application 108 may include at least one program module (e.g., program module 42) that performs functions and/or processes described herein. For example, the status application 108 may include a data module 116 that interfaces with the sensors 102, 104, 106 to obtain real time data from the sensors. In implementations, the data module 116 obtains the real time sensor data from the sensors 102, 104, 106 using an application program interface (API) of each sensor. The data module 116 may also access historical sensor data that is stored in persistent memory, such as mass storage 110. The status application 108 may include a configuration module 118 that permits a user to provide input that configures aspects of the system such as a status reporting matrix. The status application 108 may include a status rules engine (module) 120 that defines relationships between real-time sensor data, historical sensor data, and assigned IM status.

In accordance with aspects of the invention, the data module 116 collects data from the sensors 102, 104, 106 over time and stores records of this historical data in the mass storage 110. The historical data may additionally or alternatively be stored on a mobile computing device that is operatively connected to the smart watch 100, such as a smartphone that is paired with the smart watch 100. The historical data from the sensors may be used to derive baselines for a user, such as a typical resting heart rate and/or blood pressure, and the baselines may be compared to real time sensor data to determine a status of the user.

With continued reference to FIG. 2, the smart watch 100 also includes an Instant Messaging (IM) application 122, which is a program that has IM functionality that is configured to indicate a status of a user to other users of the same program. Examples of such programs include, but are not limited to, Facebook® Messenger, Skype®, and WhatsApp®, and corporate (enterprise) IM systems. In implementations, a user of the smart watch 100 may use the IM application to send and receive IM communications to and from other user devices 124a, 124b, . . . , 124n running the same IM application 122. The IM communications between devices may be transmitted via a network 126 and an IM server 128. The network 126 may be any suitable computer network such as a LAN, WAN, or the Internet. The user devices 124a-n may comprise any suitable computer devices such as smart watches, smartphones, tablet computers, laptop computers, desktop computers, etc. The IM server 128 is a computer server that is configured to coordinate IM communications between the user computer devices in a conventional manner, e.g., by having all IM client devices connect to the IM server 128 and by having all IM communications routed through the IM server 128. In embodiments, the IM server 128 also includes a status reporting matrix 130 as described in greater detail herein.

In an alternative embodiment, the smart watch 100 is not directly connected to the network 126, but rather communicates with the network through another user device. For example, the smart watch 100 may be paired with a smartphone and communicate with the smartphone using Bluetooth or NFC. The paired smartphone may communicate with the IM server 128 via the network 126 for the purpose of sending and receiving IM communications to and from the smart phone 100. In an additional embodiment, the IM application 122 is installed on the smartphone instead of the smart watch 100. In this embodiment, the IM application 122 installed on the smartphone receives a message from the IM server 128 and forwards message data to the smart watch 100.

In accordance with aspects of the invention, the status rules engine 120 is configured to determine a current status of the user of the smart watch 100 based on real time data and from at least one of the sensors 102, 104, 106. In embodiments, the status rules engine 120 obtains data in real time from one or more of the sensors 102, 104, 106, compares this data to a predefined threshold value and/or historical sensor data for this same user, and determines a status to the user based on the comparison. The real time data may be obtained from the sensors by the data module 116 and then passed from the data module 116 to the status rules engine 120. The determination made by the status rules engine 120 may be based on pre-defined rules and/or associations that are stored in the memory 28.

For example, the status rules engine 120 may compare the user's current (real time) heart rate, obtained from biometric sensors 102, to the user's baseline resting heart rate that is derived from the historical sensor data saved in storage 110. A rule utilized by the status rules engine 120 may specify that a current heart rate that is X % greater than the baseline resting heart rate indicates that the user is exercising (where "X" is any desired number defined in the rule). As such, when the status rules engine 120 determines that the user's current heart rate is X % greater than the user's baseline resting heart rate, the status rules engine 120 assigns the user's IM status as "Exercising."

The status rules engine 120 may utilize real time data from two or more of the sensors 102, 104, 106 to assign an IM status of the user. For example, the status rules engine 120 may utilize real time data from the orientation sensors 106 and real time data from the biometric sensors 102 to assign a user status such as "Sleeping." In particular, a rule utilized by the status rules engine 120 may specify that a current heart rate that is Y % less than the baseline resting heart rate, combined with a low amount of movement detected by the orientation sensors 104 indicates that the user is sleeping (where "Y" is any desired number defined in the rule). As such, when the status rules engine 120 determines that the user's current heart rate is Y % less than the user's baseline resting heart rate, and that the user is not moving, the status rules engine 120 assigns the user's IM status as "Sleeping."

Implementations of the invention are not limited to the "Exercising" and "Sleeping" examples. Instead, any desired combination of real time data from one or more sensors 102, 104, 106 may be combined with any desired historical data and any desired pre-defined rules and/or associations to assign any desired IM status. Other examples include:

"Driving"—the status rules engine 120 may be configured to assign an IM status of "Driving" based on a combination of: real time GPS data (from location sensors 104) satisfying a rule/association that indicates travel (e.g. a movement speed greater than a threshold value defined as consistent with vehicular travel), and real time user movement data (from orientation sensors 106) satisfying a rule/association that indicates driving behavior (e.g., detecting movement that is pre-defined as consistent with driving behavior, such as turning a steering wheel, operating a manual transmission, etc.).

"Travelling"—the status rules engine 120 may be configured to assign an IM status of "Travelling" based on a combination of: real time GPS data (from location sensors 104) satisfying a rule/association that indicates travel (e.g. a movement speed greater than a threshold value defined as consistent with vehicular travel), and real time user movement data (from orientation sensors 106) not satisfying a rule/association that indicates driving behavior.

"Walking"—the status rules engine 120 may be configured to assign an IM status of "Walking" based on a combination of: real time GPS data (from location sensors 104) satisfying a rule/association that indicates walking (e.g. a movement speed between threshold values defined as consistent with walking), and real time user movement data (from orientation sensors 106) satisfying a rule/association that indicates walking behavior (e.g., detecting movement that is pre-defined as consistent with walking).

"Working"—the status rules engine 120 may be configured to assign an IM status of "Working" based on the real time GPS data (from location sensors 104) satisfying a rule/association that indicates a work location. For example, the configuration module 118 may be configured to permit a user to provide input that defines a work location, and this data may be stored for use by the status rules engine 120.

"Stressed"—the status rules engine 120 may be configured to assign an IM status of "Stressed" based on the real time blood pressure data and stress level data (from biometric sensors 102) being higher than a baseline blood pressure and stress level (from historical data).

According to an embodiment of the invention, the status rules engine 120 communicates the determined status (e.g., Exercising, Sleeping, Driving, Travelling, Walking, Working, Stressed, etc.) to the IM server 128, which communicates the IM status to other user devices 124*a-n* so that the other user devices may display the determined status in the display of the IM program 120 alongside the name of the user associated with the smart watch 100. In this manner, the users of other user devices 124*a-n* that wish to send an IM communication to the user associated with the smart watch 100 are shown an IM status of the user associated with the smart watch 100 that is based on real time data from at least one of biometric sensors 102, location sensors 104, and orientation sensors 106. This provides the IM communication sender with a more accurate IM status of the intended recipient, which the sender may utilize to decide whether now is an appropriate time to the send the IM communication to the recipient.

The status rules engine 120 may communicate the determined status directly to the IM server 128, or may provide the determined status to the IM application 122 on the smart watch 100 which then passes the determined status to the IM server 128. In embodiments where the IM application 122 resides on a mobile device paired to the smart watch 100 (e.g., the IM application 122 is on a smartphone paired to the smart watch 100), the status rules engine 120 provides the determined status to the IM application 122 on the paired mobile device, which then passes the determined status to the IM server 128. The IM identity of the user (e.g., a username in the IM application 122) may be passed to the IM server 128 with the determined status of the user.

The IM status determined by the status rules engine 120 (e.g., Exercising, Sleeping, Driving, Travelling, Walking, Working, Stressed, etc.) may be referred to as a detailed IM status. In accordance with aspects of the invention, the detailed IM status may be converted to a general IM status based on the status reporting matrix 130. The IM server 128 may then provide the general IM status to the other user devices 124*a-n* for display thereon.

In embodiments, the system permits the user to configure the status reporting matrix 130 to define rules of when to provide the detailed IM status to other users, and when to convert the detailed IM status to a general IM status and provide the general IM status to other users. In implementations, the user may configure the status reporting matrix 130 to convert the IM status from detailed to general based on user lists and/or type of status. For example, the user may define a first list of users that are always provided the detailed IM status, and a second list of users for which "Exercising" and "Sleeping" are converted to "Away," "Driving" and "Stressed" are converted to "Do Not Disturb," and "Working" is converted to "Active." In this manner, when the status rules engine 120 determines the IM status of the user is "Sleeping," the IM server 128 may provide the detailed IM status ("Sleeping") to a first user of user device 124*a* and may simultaneously provide the general IM status ("Away") to a second user of user device 124*b* based on the first user being in the first list and the second user being in the second list. The first list of users and the second list of users may be defined by the user by selecting users from the user's IM contact list.

The system may be adapted to permit the user to define, via the status reporting matrix 130, which detailed IM statuses get converted to a particular general IM status. For example, a first user may define that "Exercising" and "Sleeping" are converted to "Away," while a second user may define that only "Sleeping" is converted to "Away" and that "Exercising is converted to "Active."

In another example, the user may configure the status reporting matrix 130 such that the detailed IM status "Exercising" is always converted to the general IM status "Do Not Disturb" for all users except for users contained in a particular list. In another example, the user may configure the status reporting matrix 130 to never show the detailed IM status "Sleeping" to a particular other user (e.g., a list with one user).

These examples of configuring the status reporting matrix 130 are intended to be illustrative and not limiting on implementations of the invention. Any desired rules that define when to change at least one detailed IM status to a general IM status for a list of users may be implemented with the status reporting matrix 130. In embodiments, the configuration module 118 is programmed to permit the user to provide input (e.g., at least one status rule) for configuring the status reporting matrix 130.

The status reporting matrix 130 is shown at the IM server 128 in FIG. 2. In embodiments, the IM server 128 receives the detailed IM status from the smart watch, compares the detailed IM status to the status reporting matrix 130, and converts the detailed IM status to a general IM status for one or more other users when the status reporting matrix 130 indicates the conversion is appropriate. The IM server 128 then provides the detailed IM status to a first set of users and provides the general IM status to a second set of users.

Figure 3:
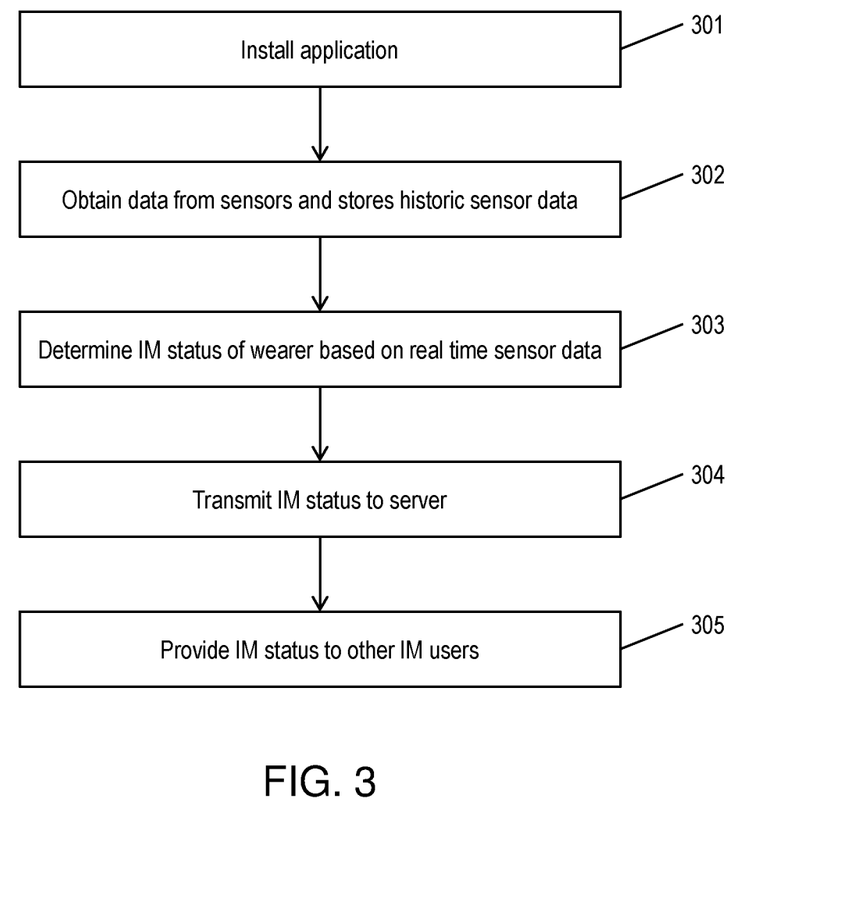
FIGS. 3 and 4 show flowcharts of methods in accordance with aspects of the invention.
Figure 4:
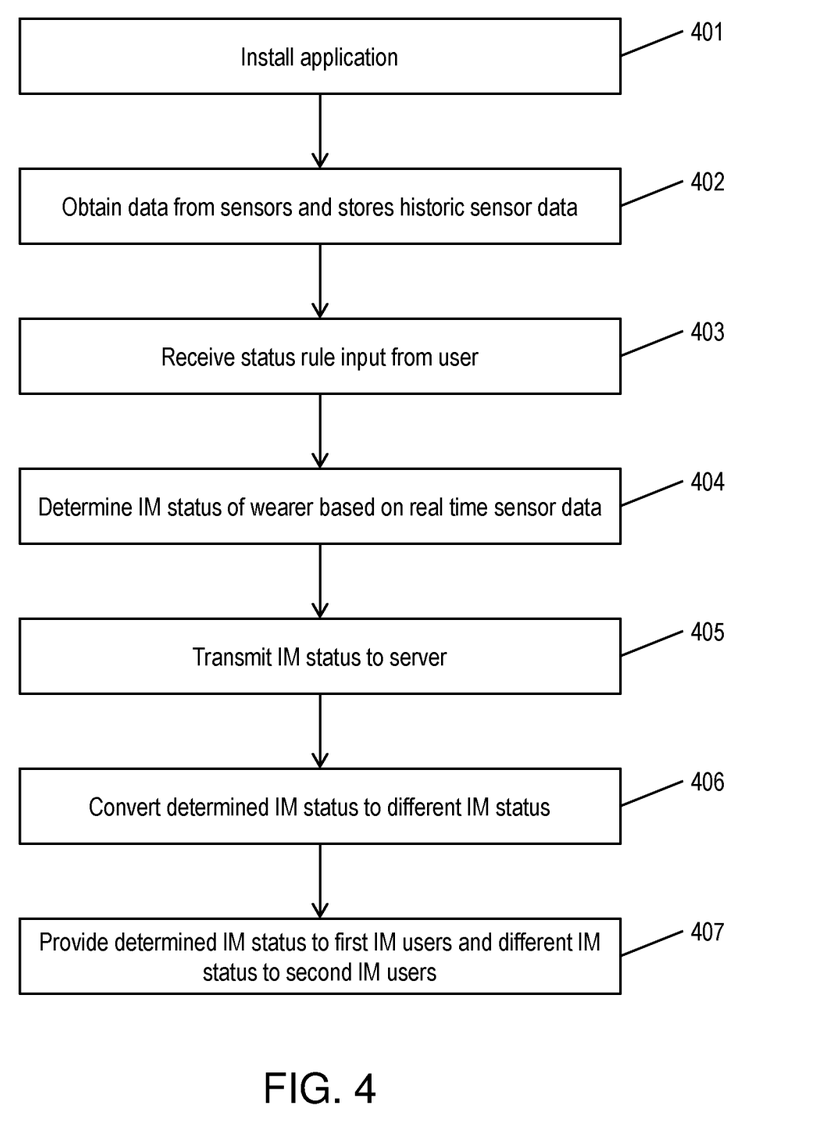

FIGS. 3 and 4 show flowcharts of methods in accordance with aspects of the invention. Steps of the methods of FIGS. 3 and 4 may be performed in the environments illustrated in FIG. 2, and are described with reference to elements shown in FIG. 2.

FIG. 3 depicts a method of determining and reporting a user's IM status based on real time sensor data of a smart watch. At step 301 a status application (e.g., IM status application 108) is installed on a smart watch (e.g., smart watch 100) including at least one of biometric sensors, location sensors, and orientation sensors.

At step 302, the status application obtains data from the smart watch sensors and stores historical sensor data. In embodiments, the status application is granted access, via an API, to the real time data generated by each of the sensors. The status application collects this data over a period of time and stores the collected data as historical sensor data. Step 302 may also include determining at least one user baseline based on the historical sensor data. For example, the status application may determine a baseline heart rate, blood pressure, or stress level of a user based on the historical sensor data. The historical sensor data, and any determined baselines, may be stored in persistent memory on the smart watch or a paired device.

At step 303, the status application determines a current IM status of a user wearing the smart watch. Step 303 may be performed in a manner similar to that described with respect to FIG. 2. In embodiments, the status application obtains real time data from one or more of the sensors (e.g., sensors 102, 104, 106), and determines the IM status of the user based on the real time sensor data. The determining may be performed using a status rules engine (e.g., status rules engine 120) including rules that define IM statuses associated with certain sensor data. In embodiments, the determining comprises comparing real time sensor data (from step 303) to at least one of: (i) historical sensor data (from step 302) and (ii) at least one pre-defined threshold. In embodiments, the comparing involves real time sensor data from two different types of sensor, e.g., GPS location and speed from location sensors 104 and user movement from orientation sensors 106.

At step 304, the status application transmits the determined IM status to an IM server (e.g., IM server 128). Step 303 may be performed in a manner similar to that described with respect to FIG. 2, e.g., via network communication.

At step 305, the IM server provides the determined IM status to other users. In embodiments, the IM server transmits the determined IM status to other user devices for display by the IM application on those devices.

FIG. 4 depicts another method of determining and reporting a user's IM status based on real time sensor data of a smart watch. At step 401 a status application is installed on a smart watch including at least one of biometric sensors, location sensors, and orientation sensors. Step 401 may be performed in the manner described with respect to step 301.

At step 402, the status application obtains data from the smart watch sensors and stores historical sensor data. Step 402 may be performed in the manner described with respect to step 302.

At step 403, the system receives status rule input from a user. In embodiments, the input at step 403 is used to define the status reporting matrix (e.g., status reporting matrix 130) that is used to convert a detailed IM status to a general IM status for specified other users of the IM application. The input may define, for example: a list of users that are provided with a detailed IM status; a list of users that are provided with a general IM status; a mapping defining which detailed IM status is converted to a respective general IM status; and a list of which detailed IM status trigger a "Do Not Disturb" mode.

At step 404, the status application determines a current IM status of a user wearing the smart watch. Step 404 may be performed in the manner described with respect to step 303.

At step 405, the status application transmits the determined IM status to an IM server. Step 405 may be performed in the manner described with respect to step 304.

At step 406, the IM server converts the determined IM status to a different IM status. Step 406 may be performed a manner similar to that described with respect to FIG. 2, e.g., using the status reporting matrix. In embodiments, the IM server uses the status reporting matrix to convert the determined (e.g., detailed) IM status to a different (e.g., general) IM status.

At step 407, the IM server provides the determined (e.g., detailed) IM status to a first set of other users, and simultaneously provides the different (e.g., general) IM status to a second set of users. In embodiments, the IM server transmits the IM status (detailed or general) to other user devices for display by the IM application on those devices.

In embodiments, a service provider, such as a Solution Integrator, could offer to perform the processes described herein. In this case, the service provider can create, maintain, deploy, support, etc., the computer infrastructure that performs the process steps of the invention for one or more customers. These customers may be, for example, any business that uses technology. In return, the service provider can receive payment from the customer(s) under a subscription and/or fee agreement and/or the service provider can receive payment from the sale of advertising content to one or more third parties.

In still additional embodiments, the invention provides a computer-implemented method for performing one or more of the processes described herein. In this case, a computer infrastructure, such as computer system 12 (FIG. 1), can be provided and one or more systems for performing the processes of the invention can be obtained (e.g., created, purchased, used, modified, etc.) and deployed to the computer infrastructure. To this extent, the deployment of a system can comprise one or more of: (1) installing program code on a computing device, such as computer system 12 (as shown in FIG. 1), from a computer-readable medium; (2) adding one or more computing devices to the computer infrastructure; and (3) incorporating and/or modifying one or more existing systems of the computer infrastructure to enable the computer infrastructure to perform the processes of the invention.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method comprising:
deriving, by a status application of a smart watch, baseline user activity data of a user from historic sensor data of the smart watch;
obtaining, by the status application of the smart watch, real time data from a sensor of the smart watch, wherein the smart watch includes a biometric sensor, a location sensor and an orientation sensor;
determining, by the status application of the smart watch, a detailed text-based instant messaging (IM) status of a user of the smart watch based on the real time data and the baseline user activity data, wherein the detailed text-based IM status is configured to be displayed to a first set of IM users to convey a detailed status of the user of the smart watch;

receiving, by the status application of the smart watch, a user input defining a general status associated with the detailed status;

transmitting, by the status application of the smart watch, the detailed text-based IM status to a computer server; and inputting, by the status application of the smart watch, at least one status rule to a reporting matrix of the computer server, wherein the status rule causes the computer server to convert the detailed text-based IM status to a general text-based IM status to be displayed to a second set of IM users to convey the general status of the user of the computing device.

2. The computer-implemented method of claim 1, wherein the determining the detailed text-based IM status is performed by utilizing pre-defined rules to determine a current condition of the user based on the real time data and the baseline user activity data, the pre-defined rules including a rule defining a relationship between the real time data, the historic sensor data, and the detailed text-based IM activity status.

3. The computer-implemented method of claim 1, wherein the real time data comprises data regarding the user's current heart rate, the baseline user activity data is data regarding the user's resting heart rate, the detailed text-based IM status relates that the user is exercising, and the general text-based IM status relates that the user is active.

4. The computer-implemented method of claim 1, wherein the determining the detailed text-based IM status further comprises comparing the real time data to a pre-defined threshold.

5. The computer-implemented method of claim 1, wherein:

the biometric sensor comprises at least one of: a heart rate monitor, a blood pressure monitor, and a stress level monitor;

the location sensor comprises a compass sensor and a global positioning system (GPS) sensor; and the orientation sensor comprises an accelerometer and a gyroscope.

6. The computer-implemented method of claim 1, wherein the status application is configured to collect and store the historic sensor data from the sensors.

7. The computer-implemented method of claim 1, wherein the real time data used in the determining the detailed text-based IM status comprises data from at least two of the sensors.

8. The computer-implemented method of claim 7, wherein the data from the at least two of the sensors comprises one of:

heart rate detected by the biometric sensor and movement detected by the orientation sensor; and moving speed detected by the location sensor and movement detected by the orientation sensor.

9. The computer-implemented method of claim 1, wherein the status application is further configured to input at least one other status rule to the reporting matrix of the computer server, the at least one other status rule causing the computer server to provide the detailed text-based IM status to a first set of IM user devices and provide the general text-based IM status to a second set of IM user devices.

10. A computer-implemented method comprising:

deriving, by a smart watch, baseline user activity data for a user from historic sensor data, the historic sensor data being obtained from sensors of the smart watch;

obtaining, by the smart watch, real time data from the sensors of the smart watch, wherein the sensors include at least one biometric sensor, at least one location sensor, and at least one orientation sensor;

determining, by the smart watch, a detailed text-based IM activity status of the user based on the real time data and the baseline user activity data by utilizing pre-defined rules to determine a current condition of the user based on the real time data and the baseline user activity data, wherein the detailed text-based IM activity status is configured to be displayed to a first set of IM users to convey a detailed status of the user;

receiving, by the smart watch, a user input defining a general status associated with the detailed status;

transmitting, by the smart watch, the detailed text-based IM activity status to a computer server for providing to the first set of IM users; and inputting, by the smart watch, at least one status rule to a reporting matrix of the computer server, wherein the status rule causes the computer server to convert the detailed text-based IM activity status to a different general text-based IM activity status to be displayed to a second set of IM users to convey a different status of the user, based on the general status defined by the user.

11. The computer-implemented method of claim 10, further comprising inputting, by the smart watch, at least one other rule to the reporting matrix of the computer server defining a list of which of a plurality of detailed IM activity status trigger a Do Not Disturb mode, whereby the different text-based IM activity status is a Do Not Disturb status generated based on the Do Not Disturb mode.

12. The computer-implemented method of claim 10, wherein the baseline user activity data is derived from historic biometric sensor data, the detailed text-based IM activity status indicates that the user is exercising or sleeping, and the user input defining the general status associated with the detailed status provides:

instructions for converting text-based IM activity status messages indicating that the user is exercising to a first general text-based IM activity status; and instructions for converting text-based IM activity status messaging indicating that the user is sleeping to a second general text-based IM activity status.

13. The computer-implemented method of claim 10, wherein the real time data comprises data regarding the user's current heart rate, the baseline user activity data is data regarding the user's resting heart rate, the detailed text-based IM status relates that the user is exercising, and the general text-based IM status relates that the user is active.

14. The computer-implemented method of claim 10, wherein the determining the detailed text-based IM status further comprises comparing the real time data to a pre-defined threshold.

15. The computer-implemented method of claim 10, wherein:

the biometric sensor comprises at least one of: a heart rate monitor, a blood pressure monitor, and a stress level monitor;

the location sensor comprises a compass sensor and a global positioning system (GPS) sensor; and the orientation sensor comprises an accelerometer and a gyroscope.

16. The computer-implemented method of claim 10, wherein a status application of the smart watch is configured to collect and store the historic sensor data from the sensors.

17. The computer-implemented method of claim 10, wherein the real time data used in the determining the detailed text-based IM status comprises data from at least two of the sensors.

18. The computer-implemented method of claim 17, wherein the data from the at least two of the sensors comprises one of:
   heart rate detected by the biometric sensor and movement detected by the orientation sensor; and
   moving speed detected by the location sensor and movement detected by the orientation sensor.

19. The computer-implemented method of claim 10, wherein the status application is further configured to input at least one other status rule to the reporting matrix of the computer server, the at least one other status rule causing the computer server to provide the detailed text-based IM status to a first set of IM user devices and provide the general text-based IM status to a second set of IM user devices.

20. The computer-implemented method of claim 10, wherein the determining the baseline user activity data comprises determining at least one of the group consisting of: a baseline heart rate of the user; a baseline blood pressure of the user; and a baseline stress level of the user.

* * * * *